(12) United States Patent
Sasso et al.

(10) Patent No.: US 8,608,779 B2
(45) Date of Patent: Dec. 17, 2013

(54) REPLACEMENT FACET JOINT AND METHOD

(76) Inventors: Ricardo C. Sasso, Indianapolis, IN (US); Kevin T. Foley, Germantown, TN (US)

(*) Notice: Subject to any disclaimer, the term of this patent is extended or adjusted under 35 U.S.C. 154(b) by 1326 days.

(21) Appl. No.: 12/137,927

(22) Filed: Jun. 12, 2008

(65) Prior Publication Data

US 2008/0249571 A1 Oct. 9, 2008

Related U.S. Application Data

(63) Continuation of application No. 10/918,541, filed on Aug. 13, 2004, now Pat. No. 7,846,184.

(51) Int. Cl.
*A61B 17/70* (2006.01)

(52) U.S. Cl.
USPC .......................................... 606/247

(58) Field of Classification Search
USPC ................................. 606/247–249
See application file for complete search history.

(56) References Cited

U.S. PATENT DOCUMENTS

| | | | |
|---|---|---|---|
| 3,741,205 A | 6/1973 | Markolf et al. | |
| 4,047,524 A * | 9/1977 | Hall | 606/75 |
| 4,502,161 A | 3/1985 | Wall | |
| 5,486,176 A | 1/1996 | Hildebrand et al. | |
| 5,527,312 A | 6/1996 | Ray | |
| 5,571,191 A | 11/1996 | Fitz | |
| 5,683,391 A | 11/1997 | Boyd | |
| 5,810,822 A | 9/1998 | Mortier | |
| RE36,758 E | 6/2000 | Fitz | |
| 6,113,637 A | 9/2000 | Gill et al. | |
| 6,132,464 A | 10/2000 | Martin | |
| 6,280,442 B1 | 8/2001 | Barker et al. | |
| 6,419,703 B1 | 7/2002 | Fallin et al. | |
| 6,485,491 B1 | 11/2002 | Farris et al. | |
| 6,485,518 B1 | 11/2002 | Cornwall et al. | |
| 6,565,605 B2 | 5/2003 | Goble et al. | |
| 6,579,319 B2 | 6/2003 | Goble et al. | |
| 6,610,091 B1 | 8/2003 | Reiley | |
| 6,974,479 B2 | 12/2005 | Trieu | |
| 7,041,136 B2 | 5/2006 | Goble et al. | |
| 7,101,398 B2 | 9/2006 | Dooris et al. | |

(Continued)

FOREIGN PATENT DOCUMENTS

| | | | |
|---|---|---|---|
| DE | 9304368.8 | * | 6/1993 |
| JP | 2002/532143 | | 10/2002 |

(Continued)

OTHER PUBLICATIONS

Translation dated Jun. 4, 2010 of G9304368.6, Vertebral Column Implant, published on Jun. 1993, Germany.*

(Continued)

*Primary Examiner* — Mary Hoffman
(74) *Attorney, Agent, or Firm* — Woodard, Emhardt, Moriarty, McNett & Henry LLP (57) ABSTRACT

Prostheses and methods for repair of a cervical facet joint. The articulating surfaces of the natural facets of the facet joint are removed only a sufficient amount to allow the insertion of flat or slightly curvilinear portions of protheses therebetween in an overlapping relationship. The portions are so inserted and the prostheses mounted by attachment to adjacent vertebrae. Also, a single natural facet may be similarly repaired with a single prosthesis.

27 Claims, 8 Drawing Sheets (56) References Cited

U.S. PATENT DOCUMENTS

| | | |
|---|---|---|
| 2002/0123806 A1 | 9/2002 | Reiley |
| 2002/0151895 A1 | 10/2002 | Soboleski et al. |
| 2003/0004572 A1 | 1/2003 | Goble et al. |
| 2003/0028250 A1 | 2/2003 | Reiley et al. |
| 2003/0171750 A1 | 9/2003 | Chin |
| 2004/0006391 A1 | 1/2004 | Reiley |
| 2004/0049273 A1 | 3/2004 | Reiley |
| 2004/0127989 A1 | 7/2004 | Dooris |
| 2004/0181229 A1 | 9/2004 | Michelson |
| 2005/0015146 A1 | 1/2005 | Louis |
| 2005/0043797 A1 | 2/2005 | Lee |
| 2005/0049705 A1* | 3/2005 | Hale et al. .................. 623/17.11 |
| 2005/0124993 A1 | 6/2005 | Chappuis |
| 2005/0131538 A1 | 6/2005 | Chervitz et al. |
| 2005/0143818 A1 | 6/2005 | Yuan et al. |
| 2005/0159746 A1 | 7/2005 | Grob et al. |
| 2006/0200137 A1 | 9/2006 | Soboleski et al. |
| 2006/0259142 A1 | 11/2006 | Dooris et al. |

FOREIGN PATENT DOCUMENTS

| | | |
|---|---|---|
| JP | 2002/532144 | 10/2002 |
| WO | WO 00/35386 | 6/2000 |
| WO | WO 00/35387 | 6/2000 |
| WO | 03/041618 A | 5/2003 |
| WO | WO 2005/072661 A1 | 8/2005 |

OTHER PUBLICATIONS

Translation dated Jun. 7, 2010 of DE10135771, Facet Joint Implant Implant, published on Feb. 2006, Germany.*
International Search Report, Application No. PCT/US 05/27469, Dated Sep. 21, 2006.

* cited by examiner

REPLACEMENT FACET JOINT AND METHOD

This application is a continuation of U.S. patent application Ser. No. 10/918,541, filed Aug. 13, 2004, which is incorporated herein by reference in its entirety.

BACKGROUND OF THE INVENTION

1. Field of the Invention

This invention relates to a method and apparatus for replacing and/or repairing a spinal facet joint particularly in the cervical spine.

2. Description of the Prior Art

Various devices and methods have been proposed for replacing the facet joints of the spine. For example, Fitz, U.S. Pat. No. RE36,758 discloses an artificial facet joint which includes a superior component that is conical or pyramidical in form and articulates with an inferior component that is also roughly conical or pyramidical in form. The U.S. patent to Gable et al., U.S. Pat. No. 6,579,319 discloses a prosthesis for the replacement of a vertebral facet joint which does not require attachment to or abutment against the posterior arch. The U.S. patent to Reiley, U.S. Pat. No. 6,610,091 discloses facet arthroplasty devices that provide articulating movement between superior and inferior prostheses. It is desirable that improved prostheses and methods be provided for replacement of the facet joints particularly in the cervical spine and particularly in the facet joints of C3 through C7.

One of the surgical operations performed on the spine involves the replacement of one or more intervertebral discs with a disc prosthesis. One of the problems involved in disc replacement is the restoration of spine alignment. It is desirable that improved methods and prostheses be made available for the restoration of spine alignment in various spinal surgeries, including those involving disc replacement.

SUMMARY OF THE INVENTION

One embodiment of the invention might involve a prosthesis for the repair of cervical facet joint which includes a superior component having a first flat or slightly curvilinear portion and a mounting portion. Also provided is an inferior component having a second flat or slightly curvilinear portion and a mounting portion. The mounting portions are adapted for connection to adjacent cervical vertebrae with the first and second portions articulating with each other between the facets of the adjacent cervical vertebrae.

Another embodiment of the invention might involve a prosthesis for the repair of a cervical facet joint. There is provided a component having a flat or slightly curvilinear portion and a mounting portion with the flat or slightly curvilinear portion being adapted for replacing the articulating surface of one of the facets of the articulating facet joint between the two adjacent cervical vertebrae.

Still another embodiment of the invention might include a method for repairing a cervical facet joint of adjacent vertebrae. A superior component is provided having a first flat or slightly curvilinear portion and a superior mounting portion. Also provided is an inferior component having a second flat or slightly curvilinear portion and an inferior mounting portion. The articulating surfaces of the facets are removed only a sufficient amount to allow the insertion of the first and second portions therebetween in an overlapping relationship. A further step involves inserting the first and second portions between the facets with the first and second portions in an overlapping relationship. Further, the components are secured to the adjacent vertebrae by attaching the mounting portions to the posterior arches of the adjacent vertebrae.

Still another method forming an embodiment of this invention involves repairing a cervical facet joint between a first vertebra and a second vertebra by providing a component having a first flat or slightly curvilinear portion and a mounting portion. The natural facet surface of the first vertebra is removed only a sufficient amount to allow the insertion of the first portion into overlapping relationship with the natural facet surface of the second vertebra. The first portion is inserted into overlapping relationship with the natural facet surface of the second vertebra and the component is secured to the first vertebra by attaching the mounting portion to the posterior arch of the first vertebra.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The invention generally relates to an artificial facet joint that is particularly configured for use in association with the cervical region of the spine. The artificial facet joint preferably includes superior and inferior components that cooperate with one another to substantially mimic normal physiological movement between the adjacent vertebrae. Implantation of the artificial facet joint does not necessarily require the removal of significant portions of the natural facet joint. Instead, the superior and inferior components are preferably configured to replace only the articulating surface portions of the natural facet joint, with the remainder of the natural facet joint remaining intact. Moreover, the artificial facet joint does not have to constitute an interbody-type device, but might instead be mounted outside of the intervertebral disc space. Additionally, the artificial facet joint may be used in association with uni-lateral or bi-lateral treatment of the cervical spine.

Figure 1:
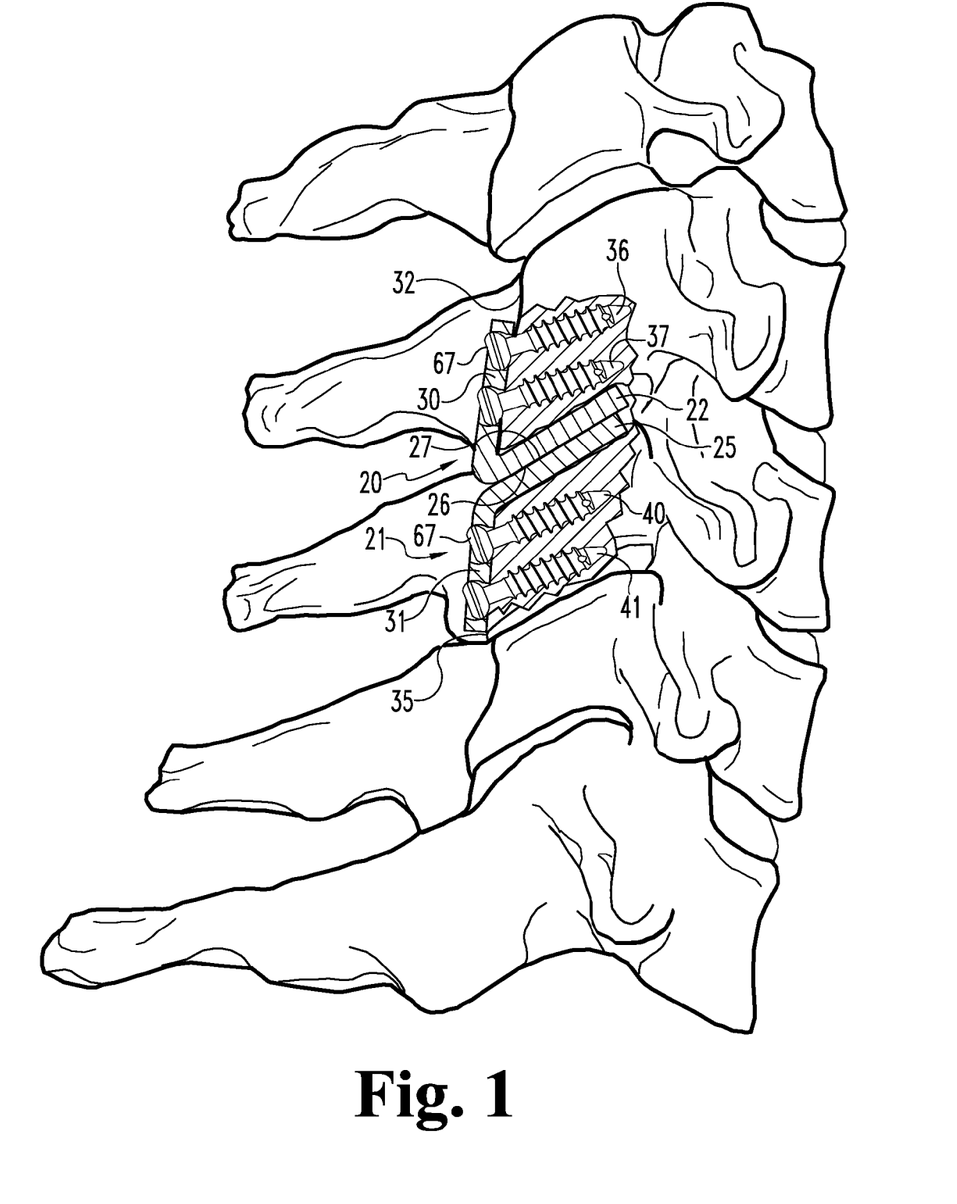
FIG. 1 is a lateral or side view of the human cervical spine with portions broken away showing one embodiment of the invention.

Referring to FIG. 1, in one embodiment, the superior component 20 and inferior component 21 each preferably include a substantially flat or slightly curvilinear articulation portion 22 and 25, respectively, defining articulating surfaces, and a mounting flange portion 30 and 31, respectively, extending transversely from the articulation portion for posterior attachment to the lateral mass 32 and 35 of respective vertebra via one or more bone screws 36, 37, 40 and 41. The articulation and mounting portions of the superior/inferior components preferably have a relatively thin, plate-like configuration. The mating articulating surfaces of the superior and inferior components of the artificial facet joint preferably are substantially planar or flat or slightly curvilinear as opposed to defining a ball-and-socket configuration. Some slight curvature in the mating articulating surfaces, while less preferred, is contemplated as within the scope of the invention. It being understood that in embodiments having both superior and inferior components, such very slight curvature is preferably matched between the two components and that such curvature may limit the extent of articulation possible. In this manner, the interface between the superior and inferior articulation portions can be described as having a "shingle" overlap arrangement.

With regard to the superior prosthetic component 20, the angle between the articulation portion 22 and the mounting flange portion 30 is preferably about 45 degrees to approximate the angular orientation of the natural inferior articular facet relative to the posterior lateral mass. Similarly, the inferior prosthetic component 21 preferably defines an angle between the articulation and mounting portions of about 135 degrees to approximate the angular orientation of the natural superior articular facet relative to the posterior lateral mass. It should be understood that the superior and inferior components of the artificial facet joint can be formed of all materials known to those of ordinary skill in the art as being suitable for this purpose. Such materials include, but are not limited to, metal, a polymer, a ceramic, or any combination thereof. It should further be understood that it is contemplated as within the scope of the invention that portions of each component might be made of one material, and other portions of a different material and/or that portions of the component might be coated with additional materials, particularly the mounting portions that might be subject to greater wear as opposing surfaces rub against one another.

Figure 2:
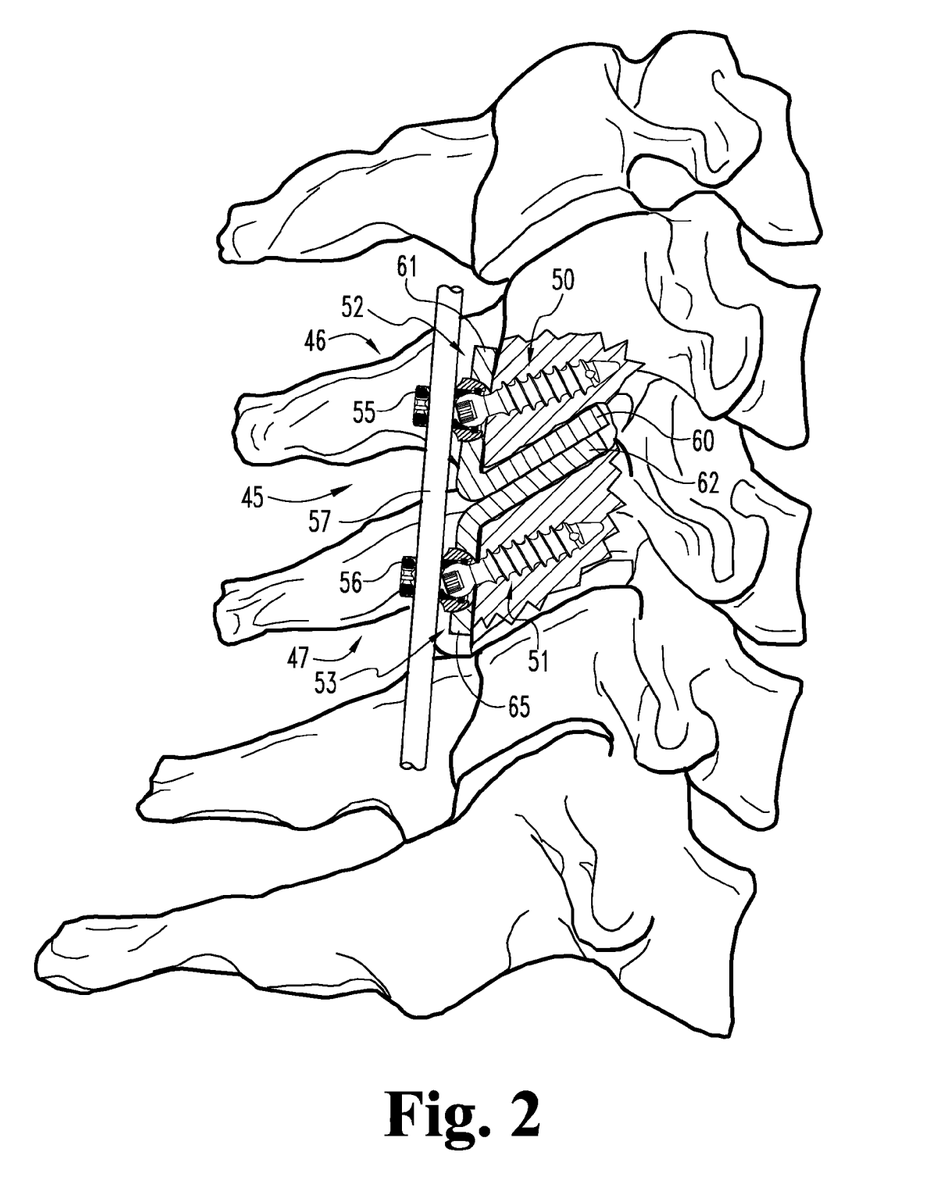
FIG. 2 is a view similar to FIG. 1 showing a further embodiment of the invention.

Referring to FIG. 2, in a further aspect of the invention, a flexible tethering system 45 is attached between, for example, the cervical vertebrae 46 and 47 to provide for flexible stabilization of the portion of the cervical spine being treated. In one embodiment, the flexible tethering system 45 might preferably include two Vertex-type screws 50 and 51 that are used to anchor the superior component 52 and inferior component 53 of the artificial facet joint to the upper and lower vertebrae, respectively. The screws 50 and 51 include receiver portions 55 and 56, respectively, that each preferably define a U-shaped channel for receiving a flexible tether 57. Flexible tether 57 is preferably a flexible rope, cable or rod. It should be understood that other types and configurations of flexible tethering systems are contemplated as within the scope of the present invention. The tethering system may be constructed and include the multi-axial bone screw assembly described and illustrated in detail in U.S. Pat. No. 6,280,442 to Barker et al. which is incorporated by reference herein. For use in the present invention, the tether 57 is preferably flexible rather than being rigid as might be required for applications in which a fixed relationship between components is desired.

Figure 3:
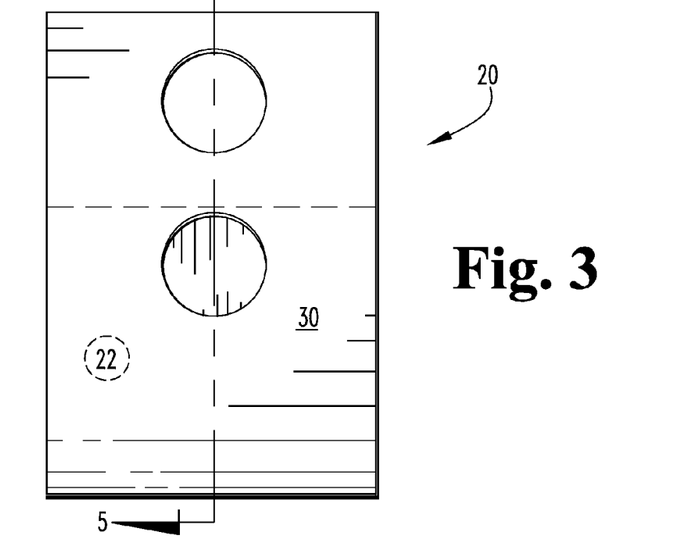
FIG. 3 is a front elevation of a superior component forming part of FIG. 1.
Figure 4:
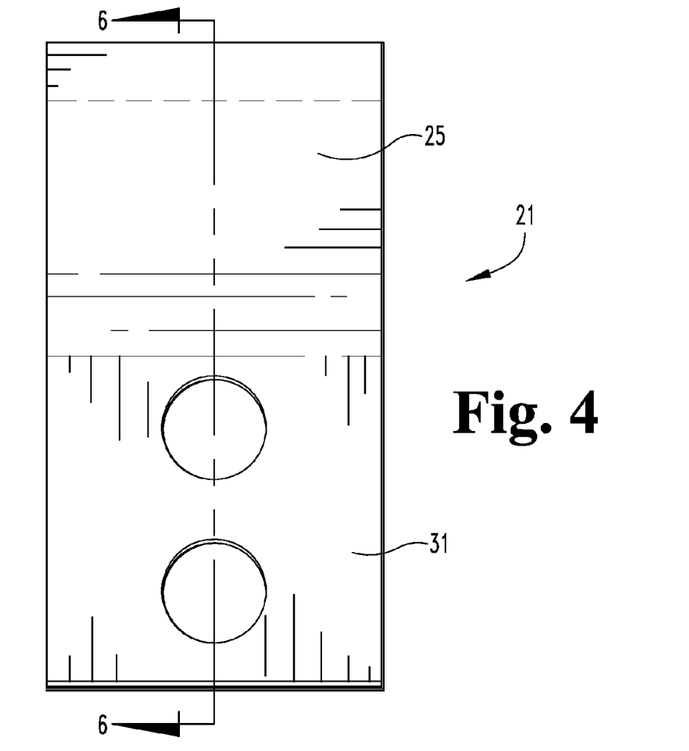
FIG. 4 is a front elevation of an inferior component forming part of FIG. 1.
Figures 5, 6:
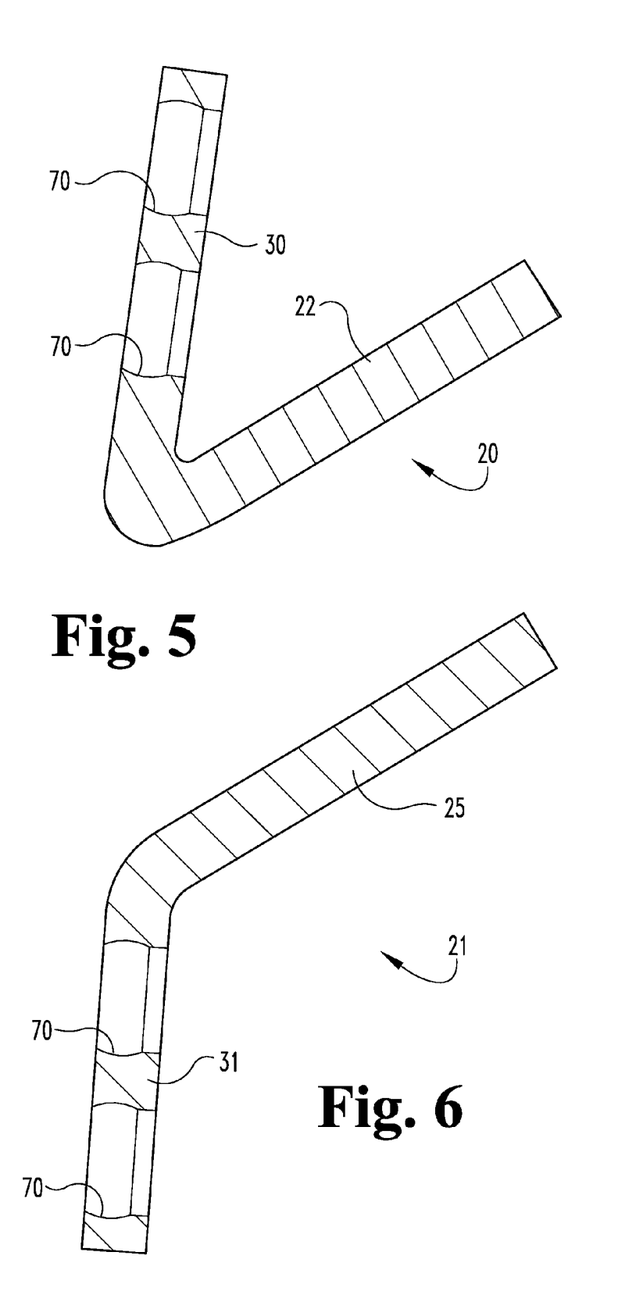
FIG. 5 is a sectional view taken in the direction of the arrows 5-5 in FIG. 3.
FIG. 6 is a sectional view taken in the direction of the arrows 6-6 in FIG. 4.

FIG. 3 is a front elevation and FIG. 5 is a section showing the configuration of the superior component 20. In one specific embodiment, the flat or slightly curvilinear articulation portion 22 and the mounting flange portion 30 are preferably arranged at an angle of 45° relative to one another. Alternatively, the angular relationship may be about 45°. FIG. 4 is a front elevation and FIG. 6 is a section showing the configuration of the inferior component 21. In one specific embodiment, the flat or slightly curvilinear articulation portion 25 and the mounting flange portion 31 are preferably arranged at an angle of 135° relative to one another. Alternatively, the angular relationship may be about 135°. The embodiments of FIGS. 1 and 2 are shown, respectively, with two screws per component and one screw per component although the number of screws in each embodiment may vary. Thus, the embodiment of FIG. 1 may use one screw per component and the embodiment of FIG. 2 may use two screws per component. It should be understood that it is contemplated as within the scope of the invention that each component may have a different number of anchors and that the number of anchors might be one, two or more than two anchors for each component.

Figure 7:
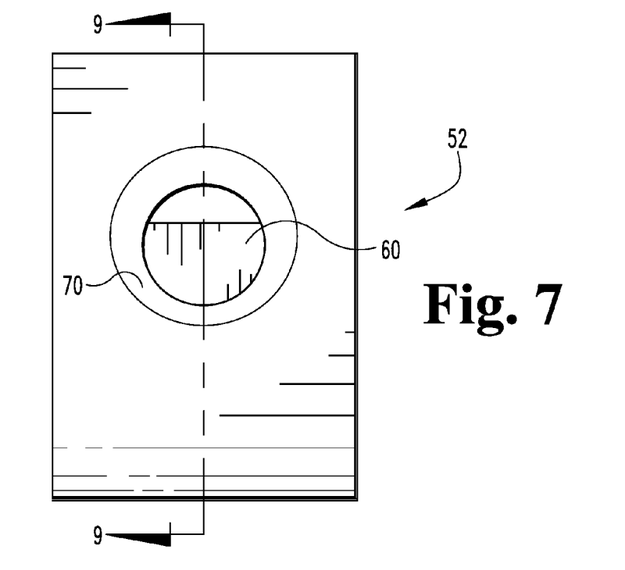
FIG. 7 is a front elevation of a superior component forming part of FIG. 2.
Figure 8:
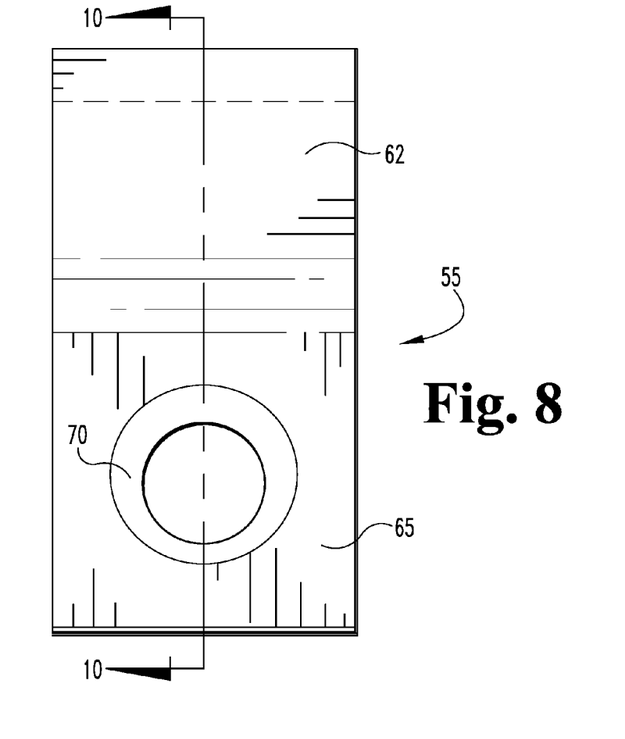
FIG. 8 is a front elevation of an inferior component forming part of FIG. 2.
Figure 9:
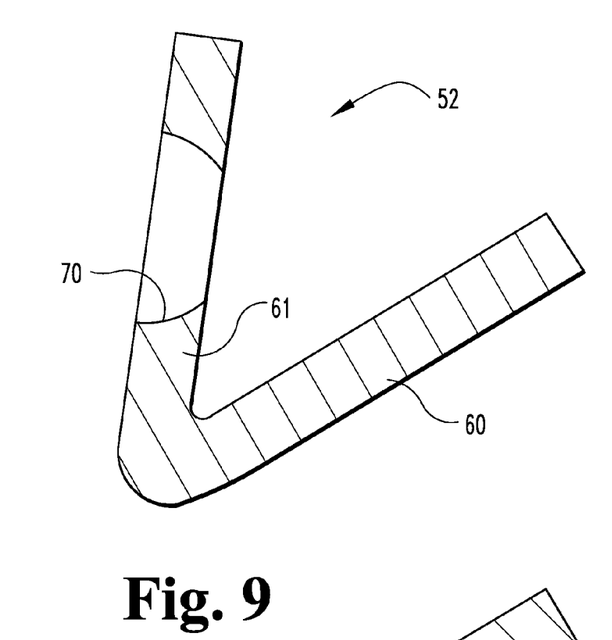
FIG. 9 is a sectional view taken in the direction of the arrows 9-9 in FIG. 7.
Figure 10:
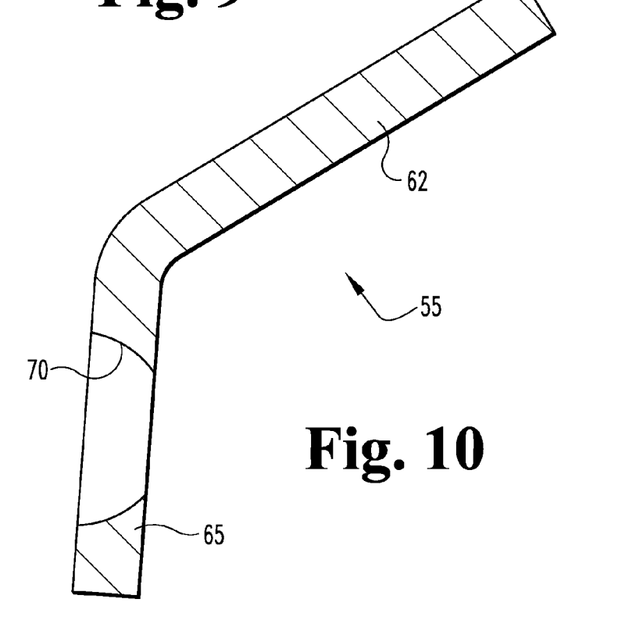
FIG. 10 is a sectional view taken in the direction of the arrows 10-10 in FIG. 8.

FIG. 7 is a front elevation and FIG. 9 is a section showing the configuration of the superior component 52. In one specific embodiment the flat or slightly curvilinear articulation portion 60 and the mounting flange portion 61 are preferably arranged at an angle of 45° relative to one another. Alternatively, the angular relationship may be about 45°. FIG. 8 is a front elevation and FIG. 10 is a section showing the configuration of the inferior component 55. In one specific embodiment, the flat or slightly curvilinear articulation portion 62 and the mounting flange portion 65 are preferably arranged at an angle of 135° relative to one another. Alternatively, the angular relationship may be about 135°.

The embodiments of FIGS. 1 and 2 are both preferably provided with mounting capabilities that allow the screw (or any other bone anchor that might be used) to attach the component to extend in the direction desired by the physician installing the component. Referring, for example, to FIG. 1, the bone screws 36, 37, 40 and 41 each preferably have rounded heads 67 that rest in rounded holes 70 (FIGS. 5 and 6) in the mounting flange portions 30 and 31. This configuration allows the surgeon to orient the screw at a variety of angles so as to place the screw in the strongest portion of the bone. This capability is also true of the multi-axial bone screw assembly of FIG. 2 as described in detail in the U.S. patent to Barker, U.S. Pat. No. 6,280,442. Thus, the bone screw holes 70 of FIGS. 7-10 are also preferably rounded to receive the heads of their respective bone screws at a range of angles.

Figure 11:
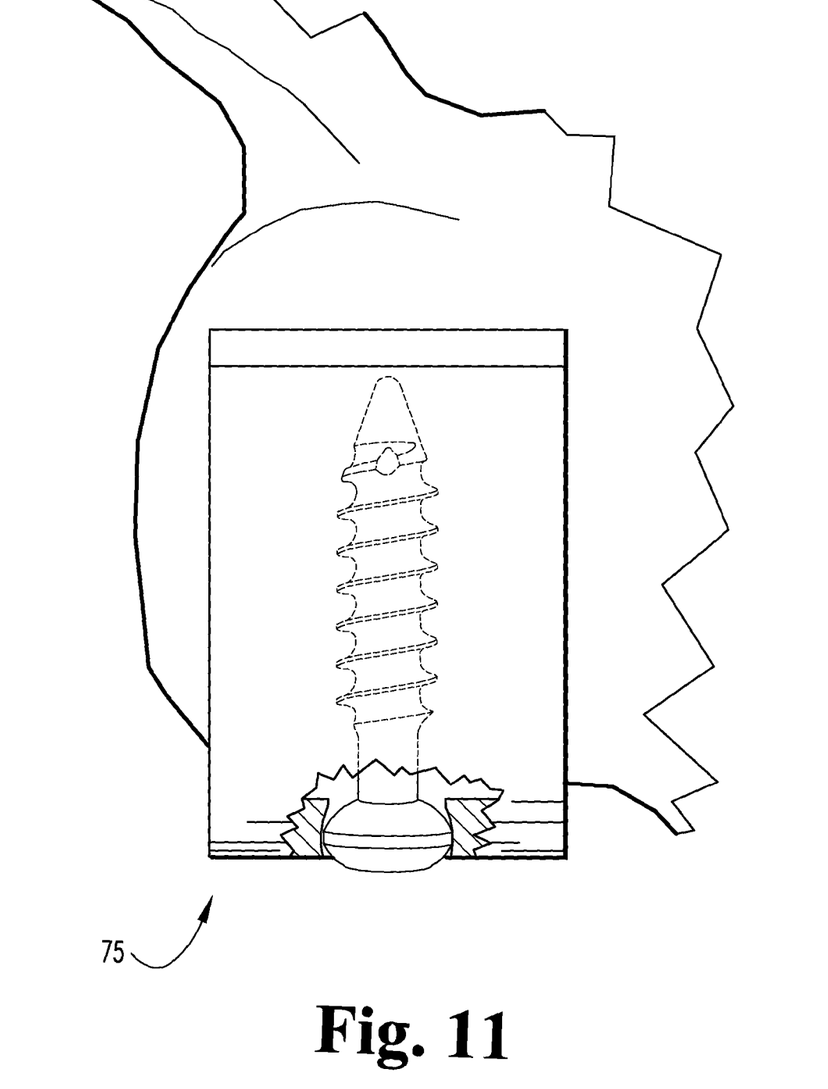
FIG. 11 is a view looking down on the facet of a cervical vertebra showing an alternative embodiment of the invention.
Figure 12:
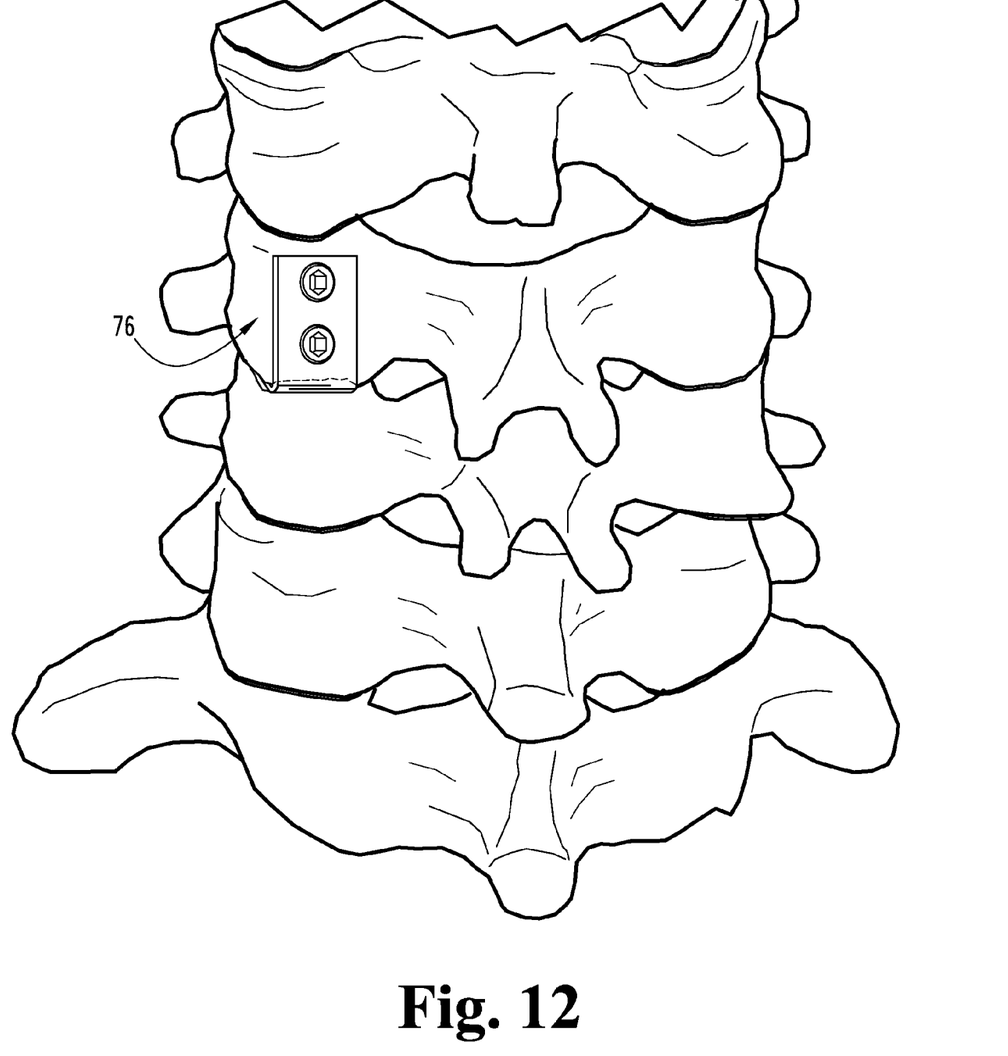
FIG. 12 is a posterior view of the cervical spine showing still another embodiment of the invention.

In certain applications, such as for example a spinal fracture, it may be appropriate to repair a cervical facet joint by replacing only one of the articulating surfaces of the natural facet joint. Thus, FIG. 11 shows a prosthesis 75 for accomplishing this purpose wherein the inferior portion of the facet joint has been replaced by the prosthesis 75 which is preferably constructed identically to the structure illustrated in FIGS. 8 and 10. FIG. 12 is a posterior view of the cervical spine and wherein the superior portion of the facet joint has been replaced by the prosthesis 76 which may preferably be constructed identically to the structure illustrated in FIGS. 3 and 5. It should be understood, however, that one or more bone screws may be used in the embodiment of FIGS. 11 and 12. Also in connection with the embodiment of FIGS. 11 and 12, it is important that the surface of the artificial articulating portion such as the surface of the portion 62 which contacts the natural facet should be made out of cartilage or biologic tissue and not be a material which causes wear on the natural facet tissue.

The method of the present invention for repairing a cervical facet joint of adjacent vertebrae involves providing a superior component having a first substantially flat or slightly curvilinear portion and a mounting portion. An inferior component is provided having a second substantially flat or slightly curvilinear portion and a mounting portion. The articulating surfaces of the natural facet joint are removed only a sufficient amount to allow insertion of the first and second portions therebetween in an overlapping relationship. The first and second portions are then inserted between the facets with the first and second portions in an overlapping relationship. The components are preferably secured to the adjacent vertebrae by attaching the mounting portions to the posterior arches of the adjacent vertebrae.

The step of removing the natural articulating surfaces of the natural facet joint can be accomplished with various surgical instruments or tools. The instrument that is used should be chosen so as to make possible effecting the exact desired dimensions of the joint. The instrument could be an oscillating saw or saws. Also, a high speed burr might be used.

In order to practice the method, preferably a guide or guides is placed into the facet joint. The guide or guides may be a flat spatula-appearing device which is placed into the joint. The guide or guides are cephalad and caudad to the center of the natural facet joint to make room to place the artificial facet joint. The guide is preferably a jig, similar to those used for total knees to cut the total knees or similar to those used in the anterior lumbar spine to cut the end plates. The jig is set up so that either an oscillating saw or a high speed burr is used to make the cuts that allow the placement of the artificial joint. Once the cuts are made, the end plates of the natural facet joint are removed so that the surgeon can look into the area where the cuts are made to make sure there are no osteophytes or any other pieces of bone that are at the tips of the natural facet joint. That is where the nerve is so the surgeon should make sure there are no big bone spurs that are deep so it should be decompressed. Once the cuts have been made preferably the surgeon will place the artificial joint as one piece with the two components married together. The artificial joint will be put in preferably as one piece. It should fit perfectly because by use of the jig to make the cuts there will be exact matching of the dimensions of the facet joint. Preferably it is put in as or similar to a press fit. Then the surgeon places the anchors or screws in to seat the artificial joint preferably with lateral mass screws. In one of the preferred embodiments, there is a tether which provides dynamic stabilization. By using the elastic tether, the facet joint is tensioned perfectly. If the procedure is done with artificial disc replacement, the artificial discs are already placed in front so that has been done first and then the tether is tensioned so that the spine is in the perfect saggittal alignment so that on a lateral x-ray, normal lordosis is achieved and confirmed. Thus, the tether (or soft rod) is used to tension this dynamic stabilizing structure and actually that will allow sliding articulation of the facet joint so that absolutely normal saggittal alignment is obtained.

In order to practice the method shown in FIGS. 11 and 12 wherein only one of the articulating surfaces of the natural facet joint is replaced, the procedure is as follows. A component is provided having a first substantially flat or slightly curvilinear portion and mounting portion. The natural facet surface of a first vertebra is removed only a sufficient amount to allow the insertion of the first portion into overlapping relationship with the natural facet surface of the second vertebra. The first portion is then inserted into overlapping relationship with the natural facet surface of the second vertebra and the component is preferably secured to the first vertebra by attaching the mounting portion to the posterior arch of the first vertebra.

It can be appreciated that the prostheses and procedures described herein make possible improved treatment of the spine. For example, these procedures may be used in combination with disc replacement in order to restore spine alignment. Further in the case of a fracture, the concepts taught herein may be used to repair a facet joint by replacing only one of the natural facet surfaces.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A method for repairing a spinal facet joint, comprising:
providing a superior component, said superior component including a first flat articulating portion and a first mounting portion, said first flat articulating portion being sized and configured for placement between the facets of a spinal facet joint;
providing an inferior component, said inferior component including a second flat articulating portion and a second mounting portion, said second flat articulating portion being sized and configured for placement between the facets of the spinal facet joint in an overlapping arrangement with said first flat articulating portion;
creating a space between the facets of the spinal facet joint for accommodating said first flat articulating portion and said second flat articulating portion in said overlapping arrangement;
inserting said first flat articulating portion and said second flat articulating portion into said space; and
attaching said first mounting portion and said second mounting portion to respective first and second lateral mass structures adjacent to the spinal facet joint such that said first flat articulating portion and said second flat articulating portion overlap and are able to slide against one another in more than one direction between the facets of the spinal facet joint,
wherein said first flat articulating portion meets said first mounting portion at an angle of about 135 degrees, and said second flat articulating portion meets said second mounting portion at an angle of about 45 degrees.

2. The method of claim 1, wherein said first flat articulating portion and said second flat articulating portion are inserted simultaneously into said space.

3. The method of claim 1, wherein said creating a space between the facets of the spinal facet joint comprises inserting a guide into the spinal facet joint.

4. The method of claim 1, wherein said creating a space between the facets of the spinal facet joint comprises removing a portion of the spinal facet joint.

5. The method of claim 4, wherein said removing a portion of the spinal facet joint comprises cutting the spinal facet joint with a cutting instrument.

6. The method of claim 5, wherein said cutting instrument is an oscillating saw.

7. The method of claim 5, wherein said cutting instrument is a high speed bur.

8. The method of claim 5, wherein said creating a space between the facets of the spinal facet joint comprises placing a cutting jig in the spinal facet joint, and wherein said cutting the spinal facet joint with a cutting instrument is carried out with the cutting jig so that the dimensions of the spinal facet joint portion removed match the dimensions of said first flat articulating portion and said second flat articulating portion in said overlapping arrangement.

9. The method of claim 1, wherein at least one of said superior component and said inferior component is comprised of a metallic material.

10. The method of claim 1, wherein at least one of said superior component and said inferior component is comprised of a polymer.

11. The method of claim 1, wherein at least one of said superior component and said inferior component is comprised of a ceramic material.

12. The method of claim 1, further comprising:
providing a flexible elongate member configured to extend along said first mounting portion and said second mounting portion when said first flat articulating portion and said second flat articulating portion are positioned between the facets of the spinal facet joint in said overlapping arrangement; and
securing said flexible elongate member to said superior component and said inferior component.

13. The method of claim 12, wherein said flexible elongate member is secured to said superior component and said inferior component before said first flat articulating portion and said second flat articulating portion are inserted into said space.

14. The method of claim 1, wherein said first articulating portion consists essentially of a first flat articulating surface, and said second articulating portion consists essentially of a second flat articulating surface; and wherein said attaching step is performed such that said first flat articulating surface and said second flat articulating surface overlap and are able to slide against one another in more than one direction between the facets of the spinal facet joint.

15. A method for repairing a spinal facet joint, comprising:
providing a superior component, said superior component including a first articulating portion and a first mounting portion, said first articulating portion being sized and configured for placement between the facets of a spinal facet joint;
providing an inferior component, said inferior component including a second articulating portion and a second mounting portion, said second articulating portion being sized and configured for placement between the facets of the spinal facet joint in an overlapping arrangement with said first articulating portion;
creating a space between the facets of the spinal facet joint for accommodating said first articulating portion and said second articulating portion in said overlapping arrangement;
inserting said first articulating portion and said second articulating portion into said space; and
attaching said first mounting portion and said second mounting portion to respective first and second lateral mass structures adjacent to the spinal facet joint such that said first articulating portion and said second articulating portion provide respective first and second opposing flat articulating surfaces touching one another, said first and second opposing flat articulating surfaces being adapted to slide against one another in more than one direction between the facets of the spinal facet joint,
wherein said first flat articulating surface meets said first mounting portion at an angle of about 135 degrees, and said second flat articulating surface meets said second mounting portion at an angle of about 45 degrees.

16. A method for repairing a spinal facet joint, comprising:
creating a space between the facets of the spinal facet joint for accommodating a first articulating portion of a superior component and a second articulating portion of an inferior component, said first articulating portion having a first flat articulating surface and being sized and configured for placement between the facets of a spinal facet joint, said inferior component including a second articulating portion and a second mounting portion, said second articulating portion having a second flat articulating surface and being sized and configured for placement between the facets of the spinal facet joint in an overlapping arrangement with said first articulating portion, in said overlapping arrangement;
inserting said first articulating portion and said second articulating portion into said space; and
attaching a first mounting portion of said superior component and a second mounting portion of said inferior component to respective first and second lateral mass structures adjacent to the spinal facet joint such that said first flat articulating surface and said second flat articulating surface overlap and are able to slide against one another in more than one direction between the facets of the spinal facet joint,
wherein said first flat articulating portion meets said first mounting portion at an angle of about 135 degrees.

17. The method of claim 16, wherein said first flat articulating portion and said second flat articulating portion are inserted simultaneously into said space.

18. The method of claim 16, wherein said creating a space between the facets of the spinal facet joint comprises placing a cutting jig in the spinal facet joint, and cutting the spinal facet joint with the cutting jig so that the dimensions of the spinal facet joint portion removed match the dimensions of said first flat articulating portion and said second flat articulating portion in said overlapping arrangement.

19. The method of claim 16, further comprising securing a flexible elongate member to said superior component and said inferior component.

20. The method of claim 19, wherein said flexible elongate member is configured to extend along said first mounting portion and said second mounting portion when said first flat articulating portion and said second flat articulating portion are positioned between the facets of the spinal facet joint in said overlapping arrangement.

21. The method of claim 19, wherein said flexible elongate member is secured to said superior component and said inferior component before said first flat articulating portion and said second flat articulating portion are inserted into said space.

22. A method for repairing a spinal facet joint, comprising:
creating a space between the facets of the spinal facet joint for accommodating a first articulating portion of a superior component and a second articulating portion of an inferior component, said first articulating portion having a first flat articulating surface and being sized and configured for placement between the facets of a spinal facet joint, said inferior component including a second articulating portion and a second mounting portion, said second articulating portion having a second flat articulating surface and being sized and configured for placement between the facets of the spinal facet joint in an overlapping arrangement with said first articulating portion, in said overlapping arrangement;

inserting said first articulating portion and said second articulating portion into said space; and attaching a first mounting portion of said superior component and a second mounting portion of said inferior component to respective first and second lateral mass structures adjacent to the spinal facet joint such that said first flat articulating surface and said second flat articulating surface overlap and are able to slide against one another in more than one direction between the facets of the spinal facet joint, wherein said second flat articulating portion meets said second mounting portion at an angle of about 45 degrees.

23. The method of claim 22, wherein said first flat articulating portion and said second flat articulating portion are inserted simultaneously into said space.

24. The method of claim 22, wherein said creating a space between the facets of the spinal facet joint comprises placing a cutting jig in the spinal facet joint, and cutting the spinal facet joint with the cutting jig so that the dimensions of the spinal facet joint portion removed match the dimensions of said first flat articulating portion and said second flat articulating portion in said overlapping arrangement.

25. The method of claim 22, further comprising securing a flexible elongate member to said superior component and said inferior component.

26. The method of claim 25, wherein said flexible elongate member is configured to extend along said first mounting portion and said second mounting portion when said first flat articulating portion and said second flat articulating portion are positioned between the facets of the spinal facet joint in said overlapping arrangement.

27. The method of claim 25, wherein said flexible elongate member is secured to said superior component and said inferior component before said first flat articulating portion and said second flat articulating portion are inserted into said space.

* * * * *